United States Patent
Tramonte

(10) Patent No.: US 6,572,373 B2
(45) Date of Patent: Jun. 3, 2003

(54) DENTAL ENDOSSEOUS IMPLANT

(76) Inventor: Silvano Umberto Tramonte, Viale Certosa 101, Milan (IT)

( * ) Notice: Subject to any disclaimer, the term of this patent is extended or adjusted under 35 U.S.C. 154(b) by 0 days.

(21) Appl. No.: 09/749,491

(22) Filed: Dec. 26, 2000

(65) Prior Publication Data

US 2002/0081553 A1 Jun. 27, 2002

(51) Int. Cl.⁷ .................................................. A61C 8/00
(52) U.S. Cl. ........................................ 433/173; 433/174
(58) Field of Search ................................ 433/173, 174, 433/175, 172, 176

(56) References Cited

U.S. PATENT DOCUMENTS

| | | | | |
|---|---|---|---|---|
| 3,708,883 A | * | 1/1973 | Flander | 433/174 |
| 3,837,080 A | * | 9/1974 | Pasqualini | 433/176 |
| 4,103,422 A | * | 8/1978 | Weiss et al. | 433/215 |
| 4,406,623 A | * | 9/1983 | Grafelmann et al. | 433/174 |
| 5,074,790 A | * | 12/1991 | Bauer | 433/174 |
| 5,205,745 A | * | 4/1993 | Kamiya et al. | 433/173 |
| 5,211,561 A | * | 5/1993 | Graub | 433/169 |
| 5,312,256 A | * | 5/1994 | Scortecci | 433/173 |
| 5,667,384 A | * | 9/1997 | Sutter et al. | 433/172 |
| 5,997,299 A | * | 12/1999 | Unger | 433/173 |
| 6,227,860 B1 | * | 5/2001 | Hobo | 433/173 |
| 6,375,465 B1 | * | 4/2002 | Engman et al. | 433/172 |

FOREIGN PATENT DOCUMENTS

| | | |
|---|---|---|
| DE | 2018330 | 10/1970 |
| DE | 2331580 | 1/1975 |
| DE | 3136602 | 8/1982 |
| DE | 4142584 | 6/1993 |

* cited by examiner

*Primary Examiner*—Kevin Shaver
*Assistant Examiner*—Melba Bumgarner
(74) *Attorney, Agent, or Firm*—Pearne & Gordon LLP

(57) ABSTRACT

A dental endosseous implant (1) is disclosed which comprises an anchoring portion (2) with a male thread intended for fitting into a respective cavity formed in the upper or lower jaw. The anchoring portion (2) is then connected by an intermediate neck (6) to a head portion (3) adapted to emerge from the osseous tissue and to define an engagement region for a superstructure in turn adapted to receive and be coupled with a tooth crown for dental restoration. The head portion (3) is advantageously of cylindrical conformation and provided with an outer male thread for receiving and being removably coupled with the superstructure. Auxiliary grip holes (8) are provided at the anchoring portion (2) to enable disengagement of said anchoring portion even in case of breaking of the intermediate neck (6); finally, a push rod (9) is removably connected with an end (2c) of the anchoring portion itself (2).

10 Claims, 2 Drawing Sheets

DENTAL ENDOSSEOUS IMPLANT

FIELD AND BACKGROUND OF THE INVENTION

The present invention relates to a dental endosseous implant.

It is known that dental endosseous implants are typically employed when it is necessary to carry out replacement of the whole root of a tooth that has reached a too high degree of decay and therefore is no longer capable of accomplishing its task.

Dental endosseous implants presently available on the market substantially consist of two different typologies.

A first type of endosseous implant, commonly known as buried implant, involves use of cylindrical elements of different sizes possibly provided with a surface working to promote anchoring of same to the bone of the patient's upper jaw (or maxilla) or lower jaw (or mandible).

These cylindrical elements are fitted into appropriate cavities to be drilled by a dentist at the point of the upper or lower jaw where the implant is to be installed. Practically, the dentist carries out opening of the mucous membrane for making a well in the patient's bone of substantially the same diameter as that of the cylinder to be fitted, then goes on fitting the implant and reclosing the mucous membrane.

Afterwards, a wait period of about 6–7 months is required to enable fresh growing of the osseous tissue that, by penetrating into the ravines provided in the cylindrical body surface, causes stabilization of said body with which said osseous tissue will form a single unit.

Once the cylindrical implant has become closely and firmly joined with the upper or lower jaws, anchoring to an end portion of said implant is made possible in order to carry out engagement of an outer structure or stump which, in turn, is adapted to receive an appropriate crown that will define the shape of an artificial tooth.

This type of implants has been widespread on the market; presently, buried implants of different shapes and sizes are available that are able to meet a variety of requirements of anatomical nature that patients may have.

In spite of the great success reached on the market by buried implants, they however have some important drawbacks.

Firstly, as briefly pointed out herebefore, typical times for setting up a buried implant are relatively long. Clearly, this is very troublesome for a patient, in particular if the osseous tissue has difficulties in regenerating and therefore the implant does not stabilize in the oral cavity.

A further drawback, as can be easily understood, is represented by the necessity to drill wells or holes for engagement of the cylindrical element in the patient's upper or lower jaws, the diametrical sizes of which must be the same as, or slightly bigger than those of said element to be fitted. In particular, the cylindrical elements used typically have a diameter of about 5 mm and therefore the diameter of the cavities formed in the patient's osseous tissue must be the same. Obviously, when installation of several implants is required or even a complete replacement of many roots, a great amount of osseous tissue is to be removed which will be a trauma for the subject submitted to this treatment.

In addition to the above drawbacks, it is also to be noted that, due to the intrinsic stiffness of the buried implants and the impossibility of carrying out deformations on the same once they have been installed, availability of a great number of implant models is made necessary for meeting all possible functional requirements.

In conclusion, it appears from the above that although buried implants require a relatively simple installation process, they however have a poor capability of being personalized upon the dentist's action, when applied, and are very traumatic for the patient both due to the relatively long times required for complete setting up of same and due to the amount of osseous tissue to be necessarily removed by a surgeon in order to carry out installation of these types of implants.

It is to be added that the buried implant does not always find an appropriate response by the patient and that consequently possible problems may bring about further delay in the installation times and still more traumas on the concerned osseous tissue.

Beside the above described buried implants, a second typology of implants, known as "Tramonte" implants, has been available on the market since many years, said implants consisting of a single monolithic piece having a threaded anchoring portion intended for screw-fitting into the patient's osseous tissue and a head portion intended for emerging from the gingival mucosa to constitute an attachment element for a tooth crown.

Typically, this type of implants requires accomplishment of holes of reduced diameters corresponding to the core of the threaded portion of the implant itself (about 2 mm) for anchoring to the patient's osseous tissue.

Once drilling has been done as well as at least partial tapping of the hole, screwing down of the anchoring portion into the hole itself is carried out until the desired axial position is reached.

Since these types of implants, due to their own nature, are self-bearing and require holes of very reduced radial dimensions, on the one hand they are immediately operative and, on the other hand, they greatly reduce traumas to be borne by the patient.

While seen from the above standpoints "Tramonte" implants appear to be advantageous, they however have been found susceptible of improvements under different points of view.

In particular, "Tramonte" implants presently on the market have predetermined structures and sizes and require a great skill and experience by the installing surgeon, for personalizing the implant depending on the subject to be submitted to treatment and the anatomical features of the latter.

In addition, in presently available implants of the "Tramonte" type, the head portion emerging from the osseous tissue has a bulky conformation that hardly lends itself to enable easy installation of possible superstructures for arrangement of crowns and the like.

It is also to be noted that typically the surgeon, once he/she has carried out installation of the implant, works on the head portion and suitably orients it depending on requirements.

This operation, if it is not carried out with appropriate care and skill, may involve breaking of the connecting neck between the head portion and the anchoring portion or at all events weakening of the connecting neck itself that during everyday use may be unable to withstand stresses transmitted to it.

It is apparent that in case of breakage of the connecting neck between the head portion and anchoring portion it is greatly problematic to carry out disengagement of the anchoring portion and therefore restoring of a new implant because the technical solutions presently available do not provide operating elements except those directly associated with the head portion.

SUMMARY OF THE INVENTION

After the above statements, the main object of the present invention is to provide a new dental endosseous implant capable of combining the positive aspects typical of "Tramonte" implants presently on the market with a greater flexibility in operation and capability of meeting the different anatomical requirements of a patient, without particular interventions and skill being called for by an installing surgeon.

It is a further object of the invention to provide a new implant which can be easily removed in case of breakage of the connecting neck between the head portion and anchoring portion of the implant itself.

Another important object of the invention is to provide an implant of easy structure and ready setting up, in which radial overall dimensions are reduced to a minimum with reference both to the head portion and the anchoring portion, without on the other hand impairing functionality and reliability of the implant itself.

The foregoing and further objects that will become more apparent in the course of the following description are substantially achieved by a dental endosseous implant comprising an anchoring portion intended for engagement in an osseous tissue of an upper jaw (or maxilla) or a lower jaw (or mandible); a head portion connected with the anchoring portion and adapted to emerge at least partly from said osseous tissue, said head portion being adapted to receive in engagement a superstructure.

BRIEF DESCRIPTION OF THE DRAWINGS

Further features and advantages will be best understood from the detailed description of some preferred but non-exclusive embodiments of a dental endosseous implant in accordance with the invention. This description will be taken hereinafter with reference to the accompanying drawings, given by way of non-limiting example, in which.

DESCRIPTION OF THE PREFERRED EMBODIMENT

Figure 1:
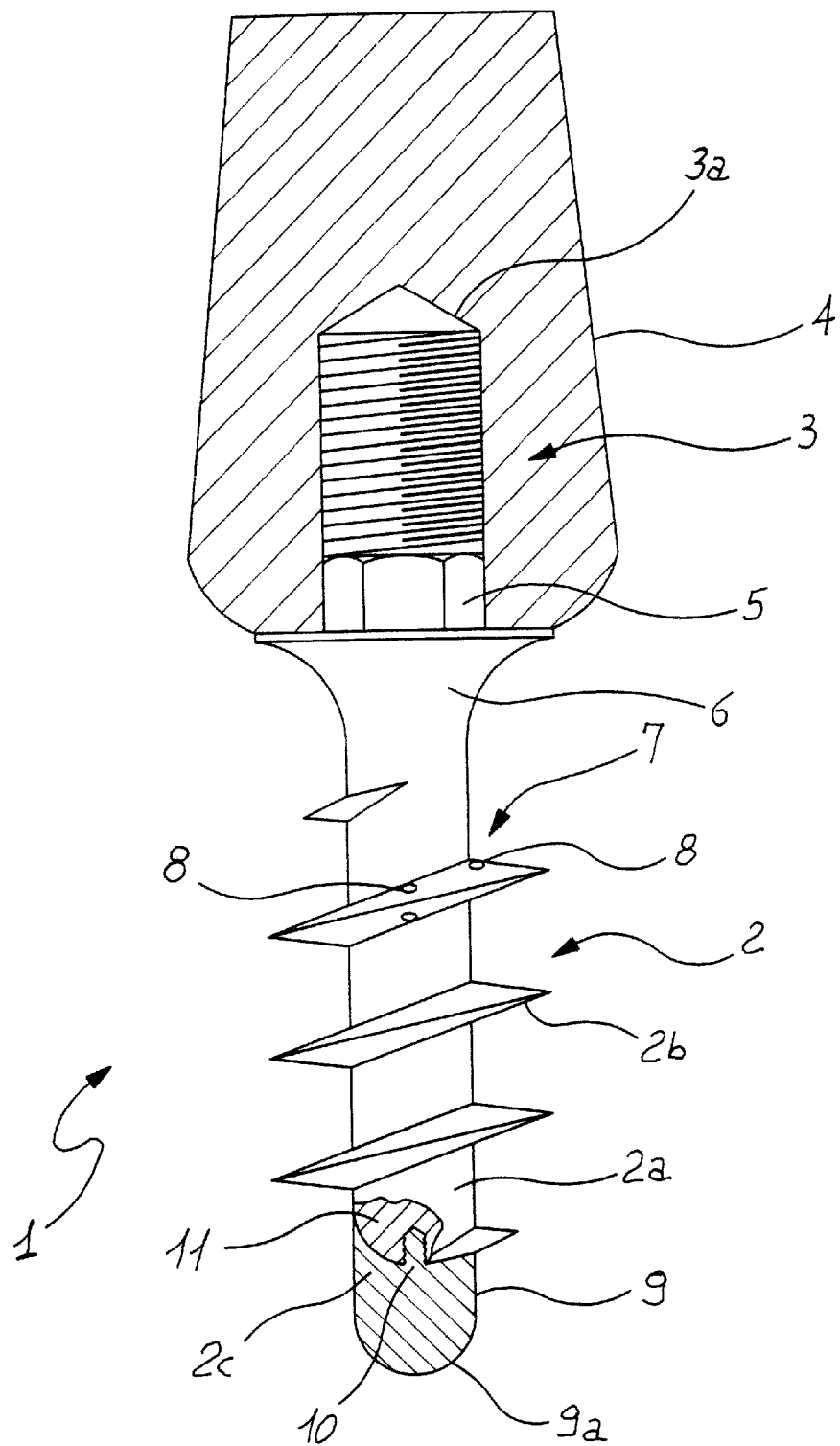
FIG. 1 is a diagrammatic longitudinal sectional view of the implant in reference.
Figure 2:
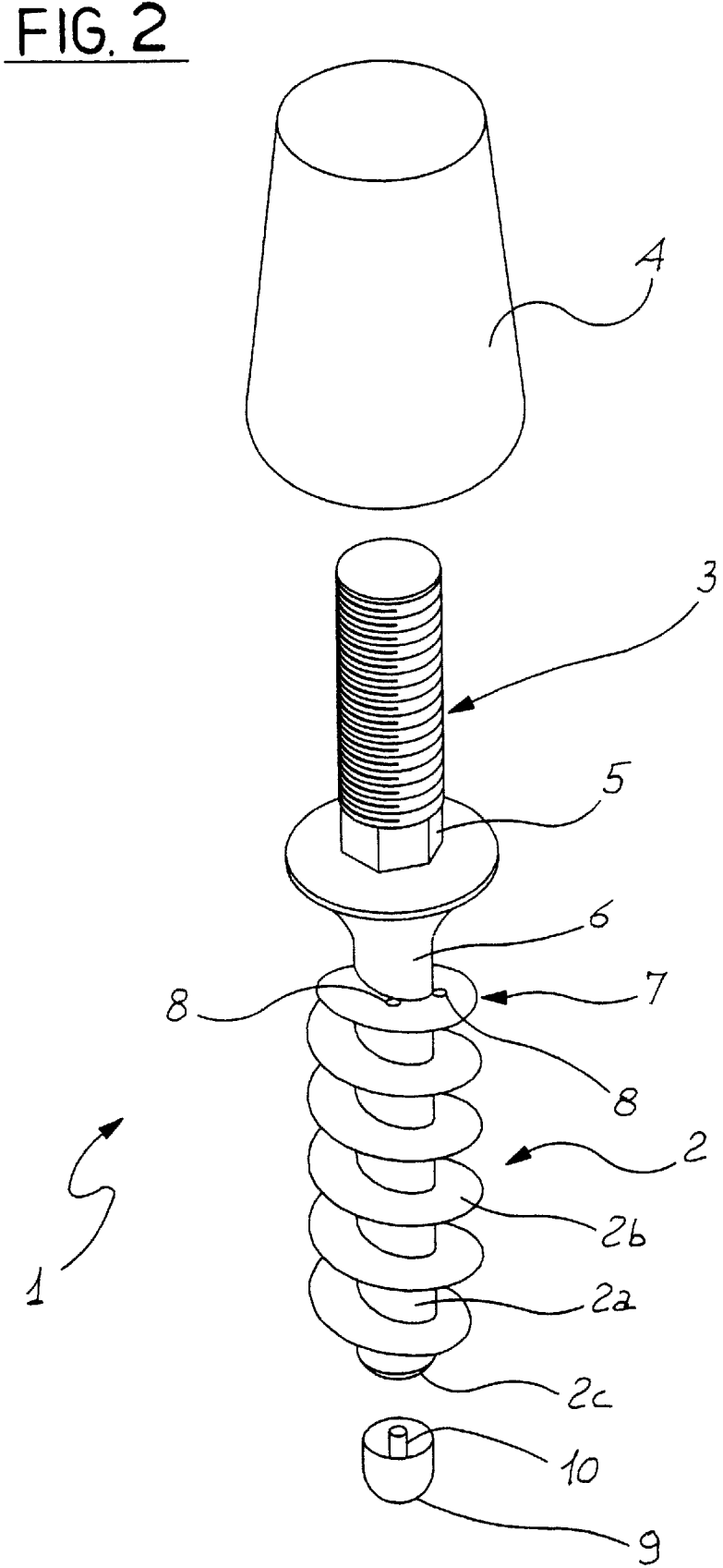
FIG. 2 is a diagrammatic exploded and perspective view of an alternative embodiment of the subject implant provided with a threaded anchoring portion the number of ridges of which is greater than that of the anchoring portion of the implant shown in FIG. 1.

With reference to the drawings, a dental endosseous implant in accordance with the present invention has been generally identified by reference numeral 1.

Implant 1 conventionally comprises an anchoring portion 2 intended for engagement in an osseous tissue of an upper or lower jaw of a patient submitted to treatment.

Connected with the anchoring portion is a head portion 3 adapted to emerge at least partly from the osseous tissue to define a grip region on which the tooth-restoring operation can be carried out.

In an original manner, the head portion has a cylindrical conformation and is advantageously provided, on an outer surface thereof, with a male thread to receive in engagement a superstructure 4 provided with a corresponding female thread.

Since the head portion 3 is made up of an externally-threaded cylindrical element, it has minimum radial overall dimensions while at the same time enabling attachment either of a superstructure selected among superstructures of the personalized type, depending on the tooth to be reconstructed and therefore the anatomy that said tooth shall have, or of a superstructure of general conformation, on which the dentist will then carry out material-removal works to obtain the most appropriate shape for the subsequent crown-applying operation.

It should be noted that by virtue of the threaded coupling between superstructure and head portion, the two parts are connected in a removable manner.

Advantageously, still for the purpose of enabling an easy setting up of the implant, the head portion comprises an operating element 5 consisting for example of a prismatic surface, such as a nut of four or more faces, coaxial with the head portion and placed at a distal position relative to the free end 3a of the head portion 3.

Looking at the accompanying drawings, it will be understood that the operating element 5 is arranged to receive a tool and, being integral with the head portion 3, can set the implant in rotation while the same is being installed when engagement of the anchoring portion 2 with the corresponding cavity formed in the patient's osseous tissue is required.

For the purpose, the anchoring portion is provided with a fixed- or variable-pitch thread consisting of one or more helices 2b placed on an outer surface of a cylindrical or slightly frusto-conical core 2a tapering away from the head portion 3.

It should be noted that advantageously helix 2b has marked radial overall dimensions. More specifically, the helix or helices 2b are wound up on core 2a and have an outer diameter greater than the core 2a diameter by approximately 30–100%.

As an alternative to the above, a knurled surface of substantially cylindrical extension placed at a position similar to that of the above described nut of four or more faces may be provided as the operating element 5 for rotation of the implant.

Surely, the solution in which an operating nut is provided is very simple from a constructional point of view, of easy operation and immediate perception by the user who, as rotation of the nut proceeds, receives from the nut faces a constant indication of the advancing state of the implant into the osseous tissue.

As shown in the figures, the anchoring portion 2 and head portion 3 are connected with each other in a unitary manner by an intermediate neck 6.

In accordance with a further advantageous aspect of the invention, the anchoring portion 2 comprises auxiliary grip means 7 substantially disposed at a starting ridge of the thread which is externally associated with the core of the same anchoring portion.

In particular, the grip means 7 comprises at least two and preferably four holes 8, extending parallelly of the axis of the anchoring portion, for example.

The different grip holes 8 are substantially angularly spaced apart the same distance from each other and disposed on the first thread ridge of the anchoring portion 2 so that, by an appropriate operating tool, rotation of the anchoring portion can be carried out.

For the purpose, holes 8 each have a corresponding access opening turned towards the head portion 3 of the implant.

Practically, even in case of breakage of the intermediate neck 6 or separation of the operating head 3 from the rest of the implant, said grip means 7 can be acted upon by an appropriate tool and extraction of the anchoring portion 2 can be carried out.

Preferably, the holes defining the auxiliary grip means are each of the through type and cross the first thread ridge, which surely promotes osteointegration of the implant into the tissue of the patient submitted to treatment.

Still with reference to said holes 8, they are displaced very close to core 2a, i.e. to the region where said helix 2b is attached to the core.

In an advantageous manner, the free end 2c of the anchoring portion 2 is rounded, preferably being in the form of a spherical cap, so that possible electrostatic charges are better distributed and the possibility that said ends 2c may penetrate through forbidden areas is diminished.

Also provided at the end 2c of the anchoring portion is a terminal rod 9 removably engaged therewith and also having a substantially smooth outer surface and a rounded end 9a preferably in the form of a spherical cap; the terminal rod 9 substantially defines a small extension of the anchoring portion core for promoting insertion of the implant during the starting steps of screwing down the anchoring portion 2 into the corresponding cavity formed in the patient's upper or lower jaw.

From a structural point of view, the terminal rod 9 is provided with a threaded shank 10 for engagement into a corresponding threaded cavity 11 arranged in the end 2c of the anchoring portion 2, so as to obtain a removable engagement therewith without impairing radial overall dimensions of the anchoring portion itself.

From a manufacturing point of view, the subject implant is preferably fully made of titanium (II), a material combining good mechanical performance with high biocompatibility.

Still from a manufacturing point of view, it should be noted that the anchoring port-on core and intermediate neck have a circular cross section of a diameter preferably included between 1.5 and 2.5 mm; the head portion, also mostly of circular section, has a core the radial bulkiness of which is around 1.5–2.5 mm too.

As regards axial extension, it is apparent that it may vary depending on requirements, and therefore on the root to be replaced by the implant and more generally on the anatomical features of the patient's concerned area. Typically, it is to be pointed out that the head portion will have an axial extension between 5 and 8 mm, the intermediate neck in turn will have an axial extension between 3 and 5 mm, and the anchoring portion an axial extension varying between 6 and 20 mm, depending on the number or ridges or threads associated therewith.

If engagement of the removable terminal rod 9 is also provided, the axial overall dimensions of the anchoring portion are to be considered increased by about 2 mm. In a preferential manner, if the anchoring portion has three ridges, the axial extension of same is about 6–7 mm plus the possible push rod; if the anchoring portion has four ridges, the axial extension of same is about 9 mm plus the possible push rod; if the anchoring portion has five ridges, its axial extension would approximately be 11–12 mm plus the possible push rod; if the anchoring portion has six ridges, its axial dimensions would approximately be 13–14 mm plus the possible push rod; finally, if the anchoring portion should have seven ridges, its dimensions would approximately correspond to 15–16 mm plus the possible push rod.

After describing the invention mainly as regards its structure, the process for setting up said implant is now briefly pointed out.

Firstly, the surgeon forms an appropriate cavity at the upper or lower jaw region to be submitted to treatment. Said cavity will have a sufficient extension or axial depth for housing the anchoring portion and its diameter will be the same as that of the anchoring portion core. Then the surgeon preferably carries out a short tapping step to facilitate operations for fitting the anchoring portion and coupling it with the respective hole.

When these steps are over, the operator selects the endosseous implant of appropriate axial dimensions and decides on whether the push rod is to be applied or not, depending on the anatomical features of the patient's oral cavity.

Subsequently, by use of the operating element, the anchoring portion can be fitted into the respective cavity and immediate fastening of the implant is thus obtained.

In a subsequent step, the operator can either possibly act on the head portion, so as to obtain an appropriate bending of the intermediate neck in the desired direction or, vice versa, directly carry out engagement of the desired superstructure.

This superstructure too may be of the personalized type i.e. based on the tooth to be restored or, alternatively, it may have a general shape to be therefore subsequently submitted to material-removal operations by the dentist.

At this point, after an impression of the head portion with the related superstructure has been obtained, a definitive crown will be applied and therefore restoration of the whole dental structure in sight will be achieved.

If during the installation steps or in use breaks should occur that jeopardize employment of the operating element, the dentist will advantageously have access to the auxiliary grip means so as to remove the anchoring portion, being thus able to carry out a new fitting of a substitutive implant.

The invention achieves important advantages.

First, the subject implant can be greatly personalized depending on requirements, both by means of deforming operations to be directly executed by the dentist and by adding possible other parts (personalized or not superstructures, terminal rod).

The particular coupling typology between the head portion and a possible superstructure is also very advantageous. In fact, this coupling is obtained due to the presence of a male thread on the head portion; since this head portion is substantially in the form of a threaded shank, it has minimum radial overall dimensions, while at the same time being very reliable when subsequent coupling with a possible superstructure is to be carried out.

In addition, as already said, the presence or not of a push rod to be removably connected to the end of the anchoring portion makes the implant adapted to be personalized for meeting the different requirements connected with the patient's anatomy.

Finally, due to the presence of the auxiliary grip means, the implant can be disengaged in a very easy manner even in case of separation of the anchoring portion from the head portion as a result of breaking.

In addition, the through holes on the first ridge defining the grip means are also elements adapted to promote a firm anchoring of the implant to the cavity arranged for the purpose in the upper or lower jaw. In fact, during the osteointegration step the osseous tissue can penetrate through said holes creating undercuts that surely increase steadiness for connection with the implant and the oral cavity.

What is claimed is:

1. A dental endosseous implant comprising:
   an anchoring portion (2) intended for engagement in an osseous tissue of an upper jaw (or maxilla) or a lower jaw (or mandible), which anchoring portion (2) includes a male threading intended for fitting into a canal previously made in the osseous tissue of the upper or lower jaw of a patient;
   a head portion (3) connected with the anchoring portion and adapted to emerge at least partly from said osseous tissue, said head portion (3) being adapted to receive in engagement a superstructure (4), said head portion (3) comprising an operating element (5) having a prismatic surface, coaxial with the implant head portion and placed at a distal position relative to a free end (3a) of the head portion and capable of receiving a tool for setting the implant in rotation during the installation step of the implant itself; and
   auxiliary grip means (7) disposed on a threading (2b) of the anchoring portion and comprising at least two holes (8) each having an axis extending parallel to a vertical axis of the anchoring portion (2) to enable the anchoring portion to be driven in rotation.

2. The dental implant as claimed in claim 1, wherein said superstructure (4) is connected in a removable manner with the corresponding head portion (3) and defines an attachment region for a dental crown.

3. The dental implant as claimed in claimed in claim 1, wherein said head portion (3) is externally provided with a male threading adapted to receive in engagement said superstructure (4) which is provided with a corresponding female threading.

4. A dental endosseous implant comprising:
   an anchoring portion (2) intended for engagement in an osseous tissue of an upper jaw (or maxilla) or a lower jaw (or mandible), which anchoring portion (2) includes a male threading intended for fitting into a canal previously made in the osseous tissue of the upper or lower jaw of a patient;
   a head portion (3) connected with the anchoring portion and adapted to emerge at least partly from said osseous tissue, said head portion (3) being adapted to receive in engagement a superstructure (4) connected in a removable manner with the corresponding head portion (3) and defining an attachment region for a dental crown, the head portion (3) comprising an operating element (5) placed at a distal position relative to a free end (3a of the head portion capable of receiving a tool for setting the implant in rotation during the installation step of the implant itself; the head portion (3) being externally provided with a male threading adapted to receive in engagement said super structure (4) which is provided with a corresponding female threading, the head portion (3) and the anchoring portion (2) of the implant being mutually connected by an intermediate connecting neck (6), the connecting neck (6) defining a rest surface for the superstructure (4), the operating element (5) being placed between the rest surface of the connecting neck (6) and the male threading of the head portion (3), the anchoring portion (2) having a core with a circular cross section of a diameter included between 1.5 and 2.5 mm;
   a push rod (9) to be removably connected with an end (2c) of the anchoring portion and presenting a threaded shank (10) intended for engagement in a corresponding threaded cavity (11) arranged in the end (2c) of said anchoring portion (2) to carry out a removable engagement therewith.

5. The dental implant as claimed in claim 4, wherein said anchoring portion (2) has a rounded end (2c) in the form of a spherical cap.

6. A dental endosseous implant comprising:
   an anchoring portion (2) intended for engagement in an osseous tissue of an upper jaw (or maxilla) or a lower jaw (or mandible), which anchoring portion (2) includes a male threading intended for fitting into a canal previously made in the osseous tissue of the upper or lower jaw of a patient;
   a head portion (3) connected with the anchoring portion and adapted to emerge at least partly from said osseous tissue, said head portion (3) being adapted to receive in engagement a superstructure (4) connected in a removable manner with the corresponding head portion (3) and defining an attachment region for a dental crown, the head portion (3) comprising a nut having an external prismatic surface with a plurality of flat faces, the nut being placed at a distal position relative to a free end (3a) of the head portion and being capable of receiving a tool for setting the implant in rotation during the installation step of the implant itself, the head portion (3) being externally provided with a male threading adapted to receive in engagement said superstructure (4) which is provided with a corresponding female threading, the head portion (3) and the anchoring portion (2) of the implant being mutually connected by an intermediate connecting neck (6), the connecting neck (6) defining a rest surface for the superstructure (4), the external prismatic surface of the nut extending between the rest surface of the connecting neck (6) and the male threading of the head portion (3), the anchoring portion (2) having a core with a circular cross section of a diameter included between 1,5 and 2,5 mm.

7. The dental implant as claimed in claim 6, wherein the dental implant comprises auxiliary grip means (7) disposed on the anchoring portion (2) to enable the anchoring portion itself to be driven in rotation.

8. The dental implant as claimed in claim 7, wherein the grip means (7) comprises at least two grip holes (8) placed on the threading (2b), said holes each having an access opening facing said head portion of the implant for receiving an operating tool, each of said holes having an axis extending parallel to a vertical axis of the anchoring portion (2).

9. The dental implant as claimed in claim 8, wherein each of said holes is a through hole.

10. The dental implant as claimed in claim 8, wherein each of said holes (8) is placed tightly close to the core (2a) of said anchoring portion (2).

* * * * *

UNITED STATES PATENT AND TRADEMARK OFFICE
CERTIFICATE OF CORRECTION

PATENT NO. : 6,572,373 B2
DATED : June 3, 2003
INVENTOR(S) : Silvano Umberto Tramonte It is certified that error appears in the above-identified patent and that said Letters Patent is hereby corrected as shown below:

Column 5,
Line 36, please delete "port-on", and insert therefor -- portion --.

Column 7,
Line 28, please delete "in claimed".
Line 48, please delete "(3a", and insert therefor -- (3a) --.

Column 8,
Line 43, please delete "1,5 and 2,5 mm", and insert therefor -- 1.5 and 2.5 mm --.

Signed and Sealed this

Fourteenth Day of October, 2003

JAMES E. ROGAN
*Director of the United States Patent and Trademark Office*